US00PP11940P2

(12) United States Plant Patent
Booman

(10) Patent No.: US PP11,940 P2
(45) Date of Patent: Jun. 19, 2001

(54) BEGONIA PLANT NAMED 'HILO HOLIDAY'

(76) Inventor: James Lawrence Booman, 2302 Bautista Ave., Vista, CA (US) 92084

( * ) Notice: Subject to any disclaimer, the term of this patent is extended or adjusted under 35 U.S.C. 154(b) by 0 days.

(21) Appl. No.: 09/375,781

(22) Filed: Aug. 17, 1999

(51) Int. Cl.[7] ..... A01H 5/00
(52) U.S. Cl. ..... Plt./343

(58) Field of Search ..... Plt./343

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Rex Begonia plant named 'Hilo Holiday', characterized by its uniform growth habit; moderate plant vigor; and interesting and attractive leaf coloration and pattern.

1 Drawing Sheet

BACKGROUND OF THE INVENTION

The present invention relates to a new and distinct cultivar of Begonia plant, botanically known as *Begonia rex* hybrid, commercially known as Rex Begonia, and hereinafter referred to by the name 'Hilo Holiday'.

The new Rex Begonia was discovered and selected by the Inventor in a controlled environment in Vista, Calif., in 1995, within a large group of seedling progeny from multiple crossings of unidentified selections of *Begonia rex* hybrids.

The selection of this plant was based on its uniform growth habit, moderate plant vigor, and attractive foliage coloration and pattern.

Asexual reproduction of the new Rex Begonia by leaf cuttings taken in a controlled environment in Vista, Calif., has shown that the unique features of this new Rex Begonia are stable and reproduced true to type in successive generations.

SUMMARY OF THE INVENTION

The cultivar 'Hilo Holiday' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Hilo Holiday'. These characteristics in combination distinguish 'Hilo Holiday' as a new and distinct Rex Begonia:

1. Uniform growth habit.
2. Moderate plant vigor.
3. Interesting and attractive leaf coloration and pattern.

In side-by-side comparisons conducted by the Inventor in Vista, Calif., plants of the new Rex Begonia differ from plants of the nonpatented cultivar Merry Christmas Corkscrew in the following characteristics:

1. Plants of the new Rex Begonia have flatter leaves than plants of the cultivar Merry Christmas Corkscrew.
2. Plants of the new Rex Begonia grow more rapidly than plants of the cultivar Merry Christmas Corkscrew.
3. Leaves of plants of the new Rex Begonia and the cultivar Merry Christmas Corkscrew differ in coloration and pattern.

4. Leaves of plants of the new Rex Begonia do not have a "corkscrew" formation whereas leaves of plants of the cultivar Merry Christmas Corkscrew have a "corkscrew" formation.

In side-by-side comparisons conducted by the Inventor in Vista, Calif., plants of the new Rex Begonia differ from plants of the nonpatented cultivar Lillium in the following characteristics:

1. Plants of the new Rex Begonia are more compact than plants of the cultivar Lillium.
2. Leaves of plants of the new Rex Begonia and the cultivar Lillium differ in coloration and pattern.

BRIEF DESCRIPTION OF THE PHOTOGRAPH

The accompanying colored photograph illustrated the overall appearance of the new Rex Begonia, showing the colors as true as it is reasonably possible to obtain in colored reproductions of this type. The photograph comprises a top perspective view of a typical plant of 'Hilo Holiday'. Foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown during the spring in Vista, Calif., under conditions which approximate commercial practice. Plants used for this description were grown in 15-cm containers for about 3 months.

Botanical classification: *Begonia rex* hybrid cultivar Hilo Holiday.

Commercial classification: Rex Begonia.

Parentage: Chance seedling of multiple crossings of unidentified selections of *Begonia rex* hybrids.

Propagation:

*Type.*—Leaf cuttings.

*Time to initiate roots, summer.*—About 56 days at 21° C.

*Time to initiate roots, winter.*—About 56 days at 21° C.

*Time to develop roots, summer.*—About 84 days at 21° C.

*Time to develop roots, winter.*—About 98 days at 21° C.

*Rooting habit.*—Fine, fibrous and well-branched.

Plant description:

*Plant form.*—Rosette; compact; dense and outwardly arching potted plant; freely basal branching with good leaf petiole strength. Vigor: moderate.

*Plant height, soil surface to top of leaf canopy.*—About 25.5 cm.

*Plant width.*—About 46 cm.

*Leaves.*—Arrangement: Simple. Length: Petiole to apex: About 15 cm. Base to apex: About 20 cm. Width: About 12.5 cm. Shape: Obliquely ovate. Apex: Acute. Base: Asymmetrically cordate. Margin: Pectinate; irregularly undulate. Texture: Leathery, rugose; pubescence on lower surface veins. Color: Young foliage, upper surface: Margin: 187A. Central venal areas: 200A to 200B. Blade: 186B to 186C, also at apex; merging into 193A. Antemarginal: Border of 146A. Young foliage, lower surface: Margin: 187A. Central venal areas: 183A to 184A. Background: 146A. Mature, fully expanded, foliage, upper surface: Margin: Brown, 187A to 200A. Central venal areas: 200A to 200B. Blade: Metallic 53B to 53C to 53D; outlined in part by 196D. Background, antemarginal: Border of 146A; iridescent blisters of 196D and 186A. Veins: 176A. Mature, fully expanded, foliage, lower surface: Margin: 187A. Central venal areas: Close to 183B; bleeding along and between veins. Background: Close to 183C. Veins: 183B; reticulate.

*Petioles.*—Length: About 14 cm. Diameter: About 7 mm. Shape: Canaliculate. Texture: Pubescent. Color: 178B to 176A.

*Stipules.*—Length: About 1.9 cm. Diameter: At base about 8 mm. Shape: Subulate, ensiform, deltoid. Color: Close to 180A.

Flower description:

*Flowering habit.*—Male flowers, single with one whorl of four tepals. Female flowers, semi-double with three tepals interior to outer whorl of five tepals. Usually about three flowers per cyme. Flowers persistent.

*Natural flowering season.*—Plants will flower continuously, but typically plants flower more abundantly during the spring and summer.

*Flowers.*—Shape: Rounded; somewhat cup-shaped. Diameter: About 3.2 cm. Depth (height): about 2.1 cm. Aspect: Drooping about 60° from vertical. Fragrance: None.

*Flower buds.*—Shape: Ovoid; bulbous with marginal lip. Length: About 1.2 cm. Diameter: About 1 cm. Color: 51B.

*Tepals.*—Arrangement: Rosette. Length: About 2 cm. Width: About 1.3 cm. Shape: Ovate with obtuse apex. Margin: Entire. Texture: Smooth, waxy; iridescent, translucent. Color: When opening, upper surface: Close to 55C. When opening, lower surface: Close to 55B. Fully opened, upper surface: Close to 55C to 55D. Fully opened, lower surface: 55A.

*Peduncles.*—Angle: About 85° from vertical. Length: About 3.5 cm. Diameter: About 2.5 mm. Strength: Firm. Texture: Smooth, waxy. Color: 146B to 146C.

*Pedicels.*—Angle: About 45° from vertical. Length: About 1.9 cm. Diameter: About 2 mm. Strength: Moderate. Texture: Smooth, waxy. Color: 137A to 179B.

*Reproductive organs.*—Male flowers: Stamen quantity: About 110, globose mass. Anther shape: Rhomboidal, lower sides curved inwardly. Anther length: About 2.5 mm. Filament length: About 2 mm. Anther color: Close to 15A. Pollen: Not observed. Female flowers: Pistil length: About 2.2 cm. Stigma shape: Funnel; bilobate. Stigma color: 163B. Ovary: Inferior; three-winged; one large top wing and two lower wings. Wings, both surfaces 147A, with 144C and 164B between wings.

Disease resistance: Plants of the new Rex Begonia have not demonstrated resistance to diseases common to Rex Begonias.

Seed production: Seed production has not been observed.

It is claimed:

1. A new and distinct cultivar of Rex Begonia plant named 'Hilo Holiday', as illustrated and described.

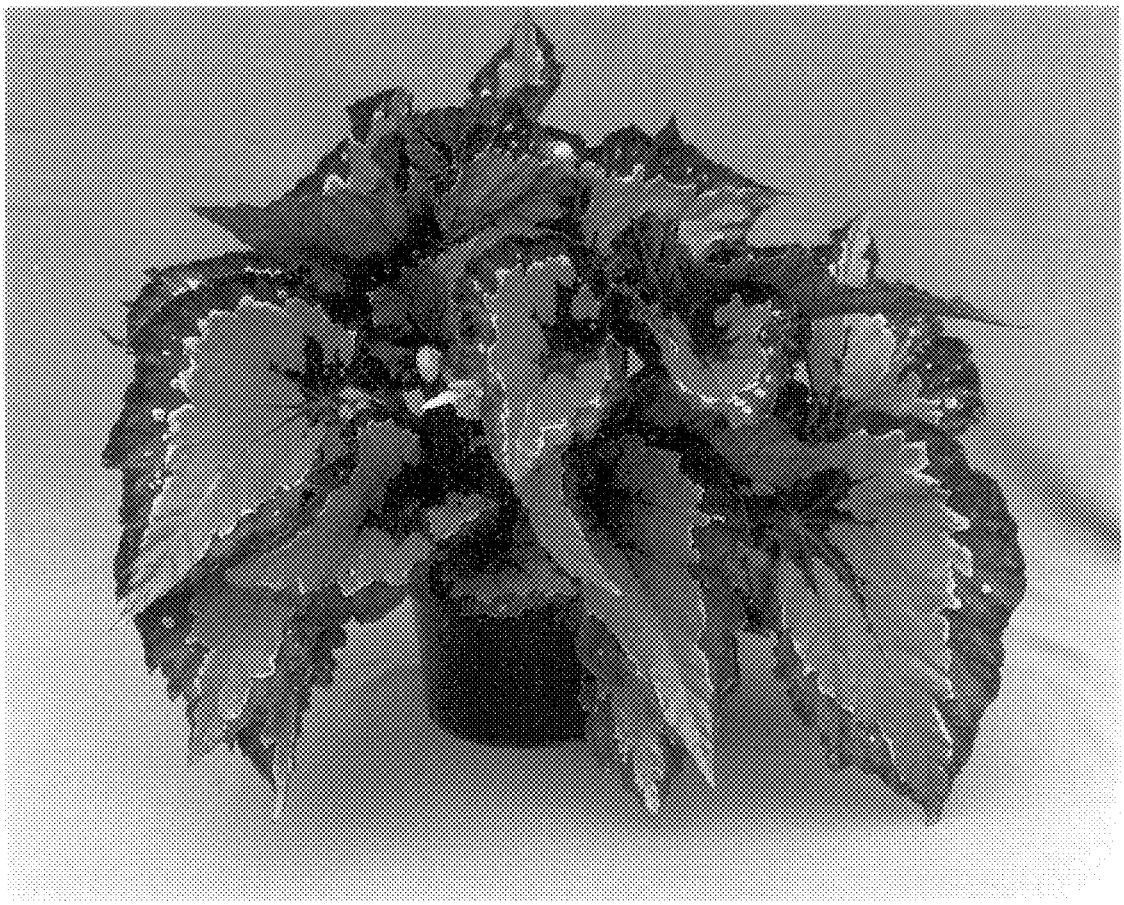

* * * * *